(12) United States Patent
Spinelli et al.

(10) Patent No.: US 9,615,976 B2
(45) Date of Patent: Apr. 11, 2017

(54) SHAPE AND PRESSURE ADJUSTABLE DRESSING FOR PUNCTURE WOUNDS

(71) Applicants: Thomas Spinelli, Northport, NY (US); Jahangir S Rastegar, Stony Brook, NY (US)

(72) Inventors: Thomas Spinelli, Northport, NY (US); Jahangir S Rastegar, Stony Brook, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 0 days.

(21) Appl. No.: 13/910,073

(22) Filed: Jun. 4, 2013

(65) Prior Publication Data

US 2013/0267881 A1 Oct. 10, 2013

Related U.S. Application Data

(63) Continuation of application No. 13/230,805, filed on Sep. 12, 2011, now abandoned, which is a continuation-in-part of application No. 13/008,881, filed on Jan. 18, 2011, now abandoned.

(51) Int. Cl.
*A61M 1/00* (2006.01)
*A61F 13/00* (2006.01)
*A61F 13/02* (2006.01)

(52) U.S. Cl.
CPC .... *A61F 13/0233* (2013.01); *A61F 13/00068* (2013.01); *A61F 13/024* (2013.01); *A61F 13/0206* (2013.01); *A61F 13/0226* (2013.01); *A61F 13/0243* (2013.01); *A61F 2013/0017* (2013.01); *A61F 2013/00536* (2013.01); *A61F 2013/00829* (2013.01)

(58) Field of Classification Search
None
See application file for complete search history.

(56) References Cited

U.S. PATENT DOCUMENTS

| | | | | |
|---|---|---|---|---|
| 4,231,357 A | * | 11/1980 | Hessner | A61F 13/02 602/47 |
| 5,052,381 A | * | 10/1991 | Gilbert et al. | 602/52 |
| 5,263,922 A | * | 11/1993 | Sova et al. | 602/59 |
| 5,580,346 A | * | 12/1996 | Spier | 602/42 |
| 5,733,251 A | * | 3/1998 | Johns | 602/57 |
| 6,656,147 B1 | * | 12/2003 | Gertsek | A61M 5/14248 604/185 |
| 7,619,130 B2 | * | 11/2009 | Nielsen et al. | 602/58 |
| 2002/0161346 A1 | * | 10/2002 | Lockwood | A61M 1/0058 604/315 |

(Continued)

*Primary Examiner* — Bradley Philips
*Assistant Examiner* — Eric Bryant

(57) ABSTRACT

A method for closing a puncture wound on skin. The method including: adhering a first surface of a first member having an unrestrained shape to the skin and over the puncture; and subsequent to the adhering, removing a second member for restraining the first member in a restrained shape from the first member. Where at least a normal force is applied to the puncture wound due to the removal of the second member from the first member which causes the first member to change towards the unrestrained shape. The removing can further cause a force substantially perpendicular to the normal force which tends to close the puncture wound.

6 Claims, 11 Drawing Sheets

(56) References Cited

U.S. PATENT DOCUMENTS

| | | | |
|---|---|---|---|
| 2003/0000521 A1* | 1/2003 | Beaudry | A61F 5/08 128/200.24 |
| 2005/0070835 A1* | 3/2005 | Joshi | A61M 1/0066 602/41 |
| 2007/0027423 A1* | 2/2007 | Scheinberg et al. | 602/54 |
| 2008/0076722 A1* | 3/2008 | Roberts et al. | 514/23 |
| 2008/0146982 A1* | 6/2008 | Rastegar et al. | 602/43 |

* cited by examiner

SHAPE AND PRESSURE ADJUSTABLE DRESSING FOR PUNCTURE WOUNDS

CROSS-REFERENCE TO RELATED APPLICATION

This application is a continuation application of U.S. application Ser. No. 13/230,805 filed on Sep. 12, 2011, which is a continuation-in-part application of U.S. application Ser. No. 13/008,881 filed on Jan. 18, 2011, the entire contents of each of which is incorporated herein by reference.

BACKGROUND

1. Field of the Invention

The present invention relates generally to dressings, and more specifically to shape and pressure adjustable dressings.

2. Prior Art

In many situations, dressings are desired to apply certain amount of pressure on the wound or apply certain amount of force to close a wound or keep it closed, sometimes over time as inflammation subsides. In other situations, it may be desired to increase the pressure or force over time to assist healing without a change in the dressing. In yet other situations it may be desirable to vary the pressure or force distribution over time. However, the currently available materials used for dressing wound are difficult if not impossible to be used to achieve the above results in general, and to achieve it with ease and in a reliable manner in particular, even with the use of such aids as elastic components or tension fixtures.

In other situations, the dressing may be required to cover certain surfaces over the body that due to the shape of the surfaces, it may be difficult to make a close fit and even more difficult to apply pressure to the surface and sustain the applied pressure over time. In such situations, the dressing has to not only conform to the covered surfaces, but at the same time may have to provide a certain pattern of pressure or force to achieve certain goals.

In the U.S. Pat. No. 7,834,232 the inventors disclose methods and means of providing dressings that can be used to apply pressure to the skin for different types of wounds to perform many of the aforementioned tasks by releasing a member from the dressing to allow the dressing to change the shape of the dressing. In situations in which a blister has formed at a location on the patient skin such as due to burn of mechanical friction or impact, etc., and in particular when the fluid collected inside the blister under the skin of the injured region is applying relatively large enough pressure to the underlying tissues that reduces and in some cases even stops blood flow to these tissues, it is highly desirable to reduce such relatively high pressures to the underlying tissues to enhance blood flow into and out of these tissues to prevent further damage to these tissues and enhance the healing process. In certain situations, the above goal is achieved by providing certain amount of relative vacuum to over the blister region. In many situations, however, it is highly desirable to relieve the pressure by puncturing the blister to allow the fluid to be discharged—at least partially—to reduce the build-up of pressure. In general, it is also highly desirable that in addition to puncturing the blister to allow the fluid discharge, certain amount of vacuum to be also applied to the region to reduce the required size of the puncture; to assist fluid discharge; and to enhance fluid flow into and out of the underlying regions of the blister. Once the blister is punctured, it is essential that the punctured blister be kept clean and medicated to prevent the possibility of infection.

SUMMARY

A need therefore exist for a method to construct dressings that can be readily applied to the blister area, and then have the capability of its shape to be varied to apply a relative vacuum (suction) to the blister area but expanding the sealed volume of the space over the covered blister area. The vacuum can be generated without any external vacuum sources.

A need also exists for a method to construct the aforementioned sealed relative vacuum (suction) forming dressing such that they could be provided with the means of puncturing the surface of the blister to allow the collected fluid to be released into the vacuum induced volume over the blister.

The aforementioned sealed relative vacuum (suction) forming dressings can also be capable of providing more than one said releasing members so that by their sequential release, the dressing shape is further changed to increase (or decrease) the said vacuum forming volumes and when desired their shape.

The aforementioned sealed relative vacuum (suction) forming dressing volume can also be provided with means to absorb the released fluid from under the blister.

The aforementioned sealed relative vacuum (suction) forming dressing volume can also be medicated to minimize the chances of infection to spread in the blister region enclosed by the dressing.

In addition, the aforementioned sealed relative vacuum (suction) forming dressing could be provided with an access through which an external vacuum source could be attached to increase the level of vacuum within the enclosed volume over the blister area and when applicable to allow the fluid to be extracted from the said enclosed volume or fluids to be added, such a medicaments or therapeutic agents.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION

Figure 1A:
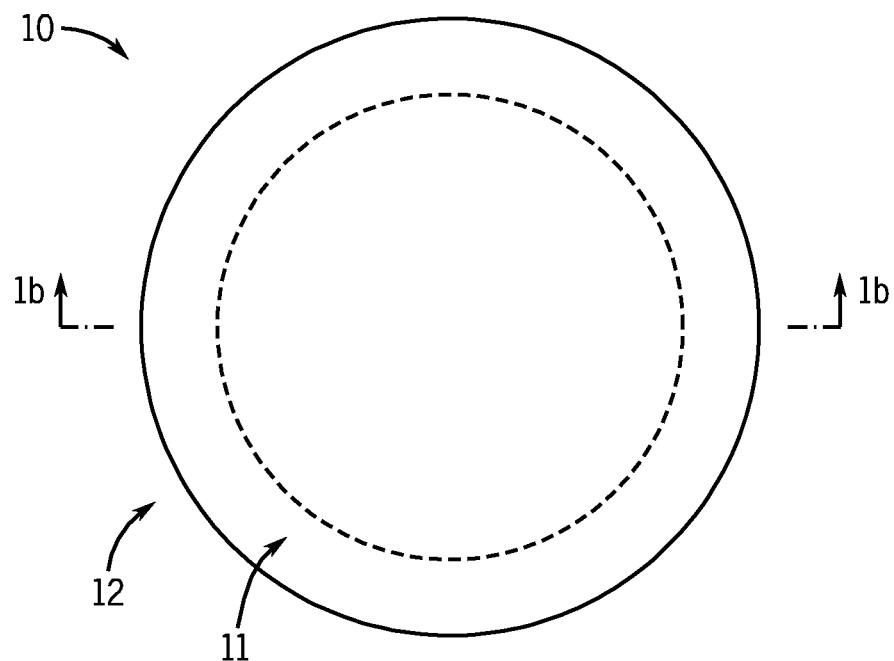
FIG. 1(a) illustrates the schematic of the top view of a first embodiment of a blister dressing having a sealed volume forming layer and at least one sealed volume increasing layer.
Figure 1B:
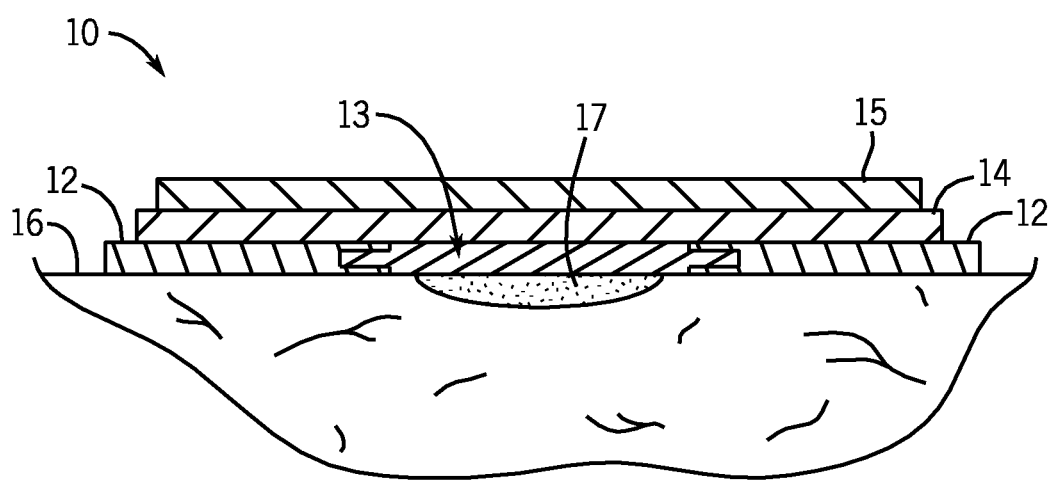
FIG. 1(b) illustrates the schematic of a cross-sectional view of the first embodiment of a blister dressing of FIG. 1(a) with a sealed volume forming layer and at least one sealed volume increasing layer intact.

A schematic of a basic design of a blister dressing is shown in the FIGS. 1(a) to 1(d). In FIG. 1(a), a top view of the blister dressing embodiment 10 is shown. It is noted that the circular shape of the sealed volume forming section 11 and the adhesive band section 12 are shown to be circular for presentation only and may take any other appropriate shape. The blister dressing 10 consists of a sealed volume forming section 11, which is surrounded by an adhesive "band" 12. The cross-sectional view A-A of the blister dressing 10 is shown in FIG. 1(b). The sealed volume forming section 11 is shown to consist of a sealed volume forming layer 13 and two layers of sealed volume increasing layer 14 and 15. The two layers are attached together and to the sealed volume forming layer 13 using any method known in the art, such as with adhesives, so that the user could readily separate them. The adhesive band 12 is permanently attached to the periphery of the sealed volume forming layer 13 using any method known in the art and may have a slight overlap to provide enough strength so that as the sealed volume forming layer deforms to generate a sealed volume, the integrity of the blister dressing 10 is ensured. When being used on a patient, the volume forming layer 13 is placed over the blister area 17, and the adhesive band 12 of the blister dressing 10 is attached to the surface of the skin 16 firmly to seal the space between the volume forming layer 13 and the blister area of the skin that it covers.

In the schematics of FIGS. 1(a)-1(d), for the sake of simplicity, only two distinct sealed volume increasing layers 14 and 15 are used. However, one or more than two such layers with different preloading patterns can be utilized in the construction of the present blister dressings. In addition, the blister dressing assembly 10 does not have to be initially flat, and may assume any appropriate shape and configuration as dictated with the particular application.

Figure 1C:
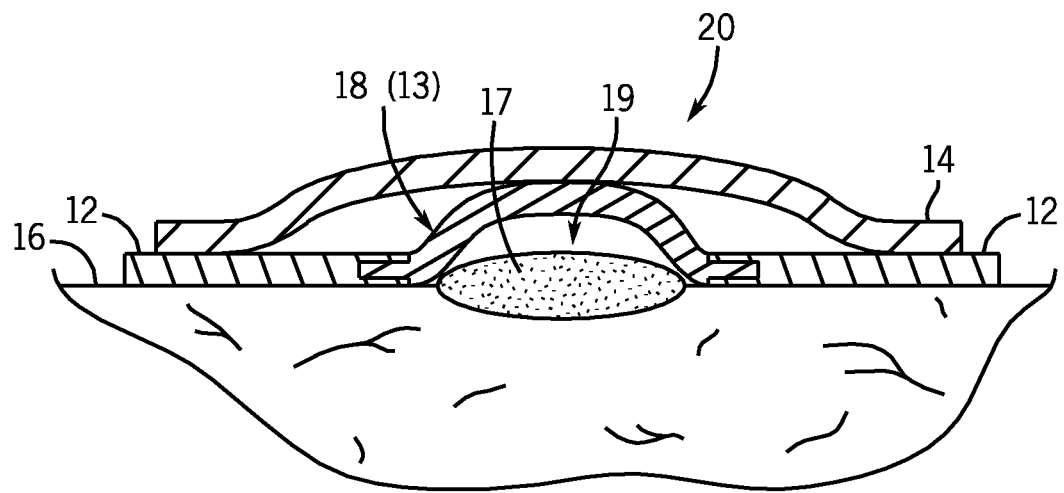
FIG. 1(c) illustrates the schematic of the schematic of the cross-sectional view of FIG. 1(b) of the first embodiment shown in FIG. 1(a) with the first sealed volume increasing layer removed and the resulting change in the shape of the sealed volume forming layer to yield larger sealed volume over the enclosed blister area.

Once the blister dressing 10 is applied to the skin 16 over the blister 17 and the adhesive band 12 is attached over the skin to seal the space between the blister 17 and the covering surface of the sealed volume forming layer 13, the first sealed volume increasing layer 15 may be removed to increase the said sealed space between the blister 17 and the covering surface of the sealed volume forming layer 13. Once the first sealed volume increasing layer 15 is removed, the mechanical potential energy stored in the sealed volume forming layer 13 is partially released as described later in this disclosure, allowing the sealed volume forming layer 13 to take the shape (dome-shaped) 18 as shown in FIG. 1(c), thereby causing the space between the blister 17 and the covering surface of the sealed volume forming layer 18 (13 in its pre-release configuration) to be increased to form the space 19. The resulting increase in the volume of the space between the blister 17 and the covering surface of the sealed volume forming layer 18 to form the space 19 will also generate a relative vacuum within the sealed space 19. It is appreciated by those familiar with the art that as the sealed volume forming layer 13 is deformed following removal of the first sealed volume increasing layer 15, the second sealed volume increasing layer 14 may slightly deform as shown in FIG. 1(c) and form a bulge 20.

Figure 1D:
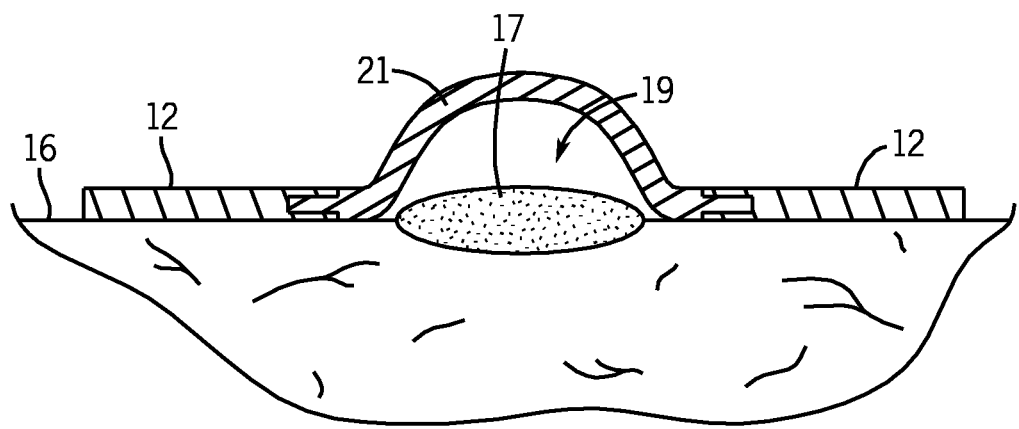
FIG. 1(d) illustrates the schematic of the cross-sectional view of FIG. 1(b) of the first embodiment shown in FIG. 1(a) with a second sealed volume releasing layer removed and the resulting change in the shape of the sealed volume forming layer to yield even larger sealed volume over the enclosed blister area.

When a higher level of relative volume is desired to be generated within the space 19 over the area of the blister 17, the second sealed volume increasing layer 14 may be removed to further increase the sealed space 19 between the covered area of the blister 17 and the covering surface of the sealed volume forming layer 21 (indicated by numeral 18 in FIGS. 1(c) and 13 in FIG. 1(b)) as shown in FIG. 1(d). Once the second sealed volume increasing layer 14 is removed, the mechanical potential energy still stored in the sealed volume forming layer 18 (FIG. 1(c)) is further released as described later in this disclosure, allowing the sealed volume 17 to further increase as shown in FIG. 1(d), thereby causing the level of relative volume to further increase in the sealed volume 17.

In one embodiment, on at least a portion of the surface area under the volume forming layer 13, such as extending over and certain amount past blister area 17 as shown in FIG. 1(b), is provided with a layer of fluid absorbent material 22 to absorb the discharged fluid that is collected in the blister once it is released. The absorbent material 22 can also be medicated to prevent the chances of infection in the blister area, particularly following the rupture of the blister skin and discharging of the collected fluid.

As discussed below, the material of the volume forming layer 13 can be such that it has the shape as indicated in FIG. 1(d) but is restrained into a different shape, such as a flat shape as shown in FIG. 1(a) by the volume increasing layers 14, 15. As the volume increasing layers are removed, the restraint is also removed, allowing the volume forming layer 13 to take a different shape. Such materials can be fabrics, plastics or metals and can be formed integrally or separately from the adhesive band 12. When formed separately, the volume forming layer 13 and adhesive band 12 can be attached by any means known in the art, such as heat welding, adhesive and the like.

Figure 2:
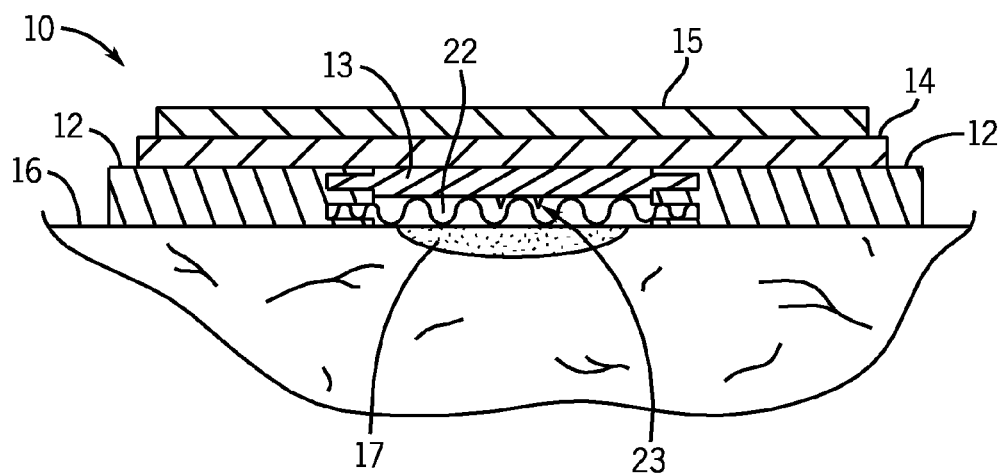
FIG. 2 illustrates the schematic of the cross-sectional view of the first embodiment of a blister dressing of FIG. 1(a) shown in FIG. 1(b) with an added fluid absorbent layer below the sealed volume forming layer and at least one sealed volume increasing layer intact.

In another embodiment, at least one sharp puncturing tip 23 is provided over the surface under the volume forming layer 13 as shown in FIG. 2, such as extending at least partially through the fluid absorbent material layer 22 (when the dressing 10 is provided with a fluid absorbent layer 22). The user would then attach the blister dressing 10 over the blister area 17 such that the puncturing tip(s) 23 is over the surface of the blister. Then when desired, by pressing over the surface of the sealed volume increasing layer 15, FIG. 2, the surface skin of the blister 17 is punctured, allowing the collected blister fluid to begin to be discharged. It is appreciated that the aforementioned puncturing of the blister skin may be performed following removal of the first sealed volume increasing layer 15 or after the second sealed volume increasing layer 14 has also been removed.

In the embodiments of FIGS. 1-2, particularly when the blister dressing is provided with blister puncturing tip(s) 23, FIG. 2, the material used to construct the volume forming layer 13 can be transparent, e.g., fabricated with a transparent medical grade plastic material. This is also the case for the first and second sealed volume increasing layers 15 and 14 and the adhesive band 12. As a result, the user can more accurately position the volume forming layer 13 and its puncturing tip(s) 23 over the surface of the blister 17. The fluid absorbent material layer 22 may also be provided with holes to allow the user to more accurately locate the dressing over the blister.

It will be appreciated by those skilled in the art that the area around the puncturing tip(s) 23 of the fluid absorbent material layer 22 may be provided with local anesthetic medication so that the blister puncturing action becomes painless to the patient.

The sealed volume forming layer 13 can be originally shaped essentially as shown in FIG. 1(d) and indicated by numeral 21, but has been elastically "flattened" (or brought to any other desired shape) and held in the flattened configuration (thereby resulting in a stored mechanical potential energy in the sealed volume forming layer 13, which when released would tend to bring the sealed volume forming layer 13 to its aforementioned original shape) by the sealed volume increasing layers 14 and 15. Obviously, if the sealed volume increasing layers 14 and 15 are separated from the blister dressing assembly 10, as shown in FIG. 1(d), sealed volume forming layer 13 would return to their original shape shown in FIG. 1(d) and indicated by numeral 21.

It will be appreciated by those skilled in the art that the sealed volume forming layer 13 can be designed in numerous ways, a few of which are described later in this disclosure, such that the aforementioned mechanical potential energy that is stored in the sealed volume forming layer 13 when it is flattened to the configuration shown in FIG. 1(b) is due to for example tensile or compressive or torsion or flexural bending or their combination induced potential energy.

Figure 3A:
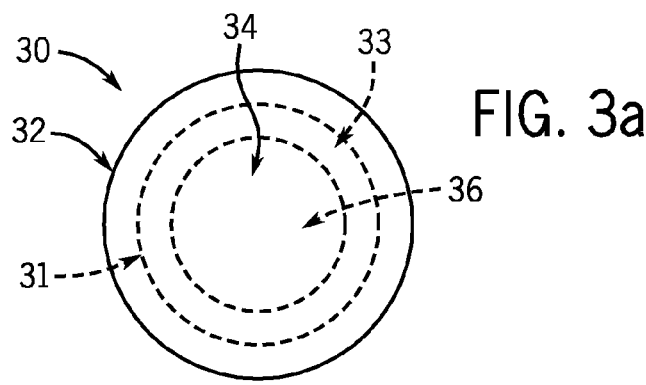
FIG. 3(a) illustrates the schematic of the top view of another embodiment of a blister dressing having a sealed volume forming layer and at least one sealed volume increasing layer.
Figure 3B:
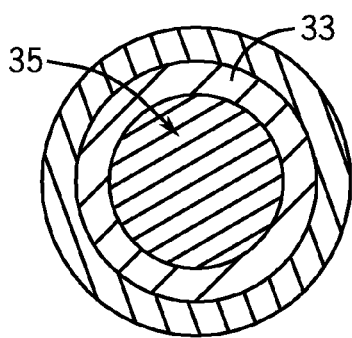
FIG. 3(b) illustrates the schematic of the top view of the embodiment of FIG. 3(a) following removal of a first sealed volume increasing layer.
Figure 3C:
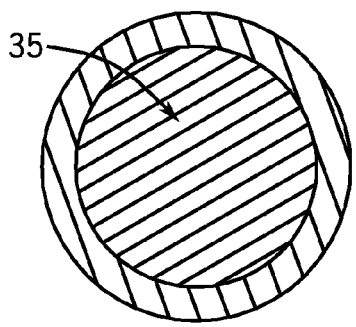
FIG. 3(c) illustrates the schematic of the top view of the embodiment of FIG. 3(a) following removal of a second sealed volume increasing layer.

As an example, consider the blister dressing embodiment 10 of FIG. 1(a), which is redrawn in FIG. 3(a) and indicated by numeral 30, with the sealed volume forming section 11 (in FIG. 3(a) indicated by numeral 31) and the adhesive band section 32. The sealed volume forming section 31 consists of at least one sealed volume increasing layer in general, and in the case of the blister dressing embodiment 30 shown in FIG. 3(a), a first (top) sealed volume increasing layer 34 and a second sealed volume increasing layer 33. Under the sealed volume increasing layers 33 and 34, a sealed volume forming layer 35 (shown in FIGS. 3(b) and 3(c) but not visible in the top view of FIG. 3(a)) is provided which is attached to the adhesive band section 32 as previously was described for the embodiments of FIGS. 1(a)-1(d). In FIG. 3(a)-3(c) the sealed volume increasing layers 34 is considered to be positioned inside a provided (circular) opening 36 inside the sealed volume increasing layer 33, but can overlap the sealed volume increasing layer 33 to ease its removal by the user. The sealed volume increasing layer 33 is considered to be positioned over the (circular) sealed volume forming layer 35 as shown in FIG. 3(c), but is preferably overlapping the adhesive band section 32 to ease its removal by the user.

Figure 3D:
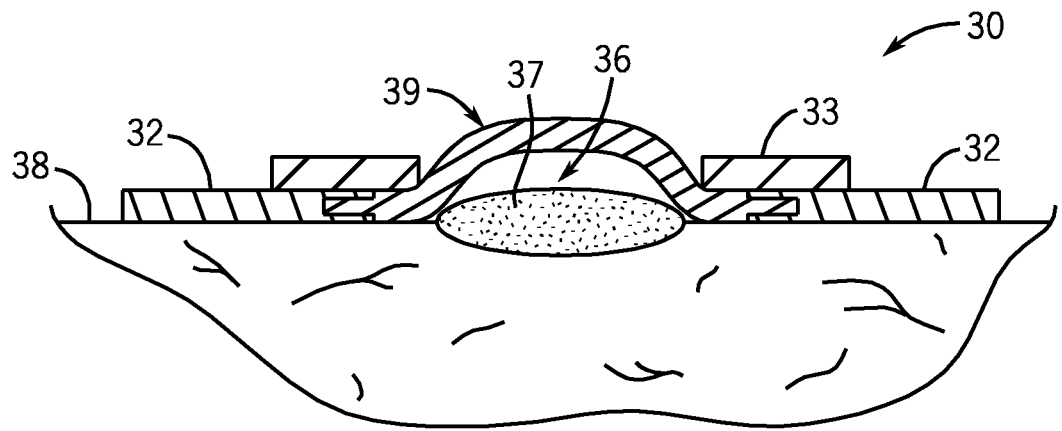
FIG. 3(d) illustrates the schematic of a cross-sectional view of the embodiment of FIG. 3(a) following removal of a first sealed volume increasing layer and forming of a space above the blister area with relative vacuum.
Figure 3E:
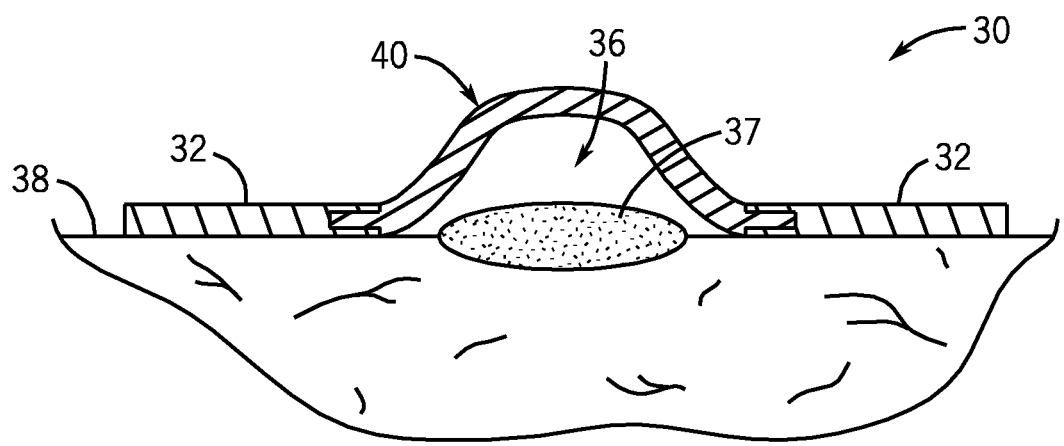
FIG. 3(e) illustrates the schematic of a cross-sectional view of the embodiment of FIG. 3(a) following removal of a second sealed volume increasing layer to further increase the volume of the space formed above the blister area and the generated relative vacuum.

In use, the blister dressing is attached over the blister 37 to the surface of the skin 38 as was described before for FIG. 1(b) and shown in FIG. 3(d). The first (top) sealed volume increasing layer 34 (FIG. 3(a)) is then removed (FIG. 3(b)), causing the underlying portion of the sealed volume forming layer 35 to form a volume 36 above the blister 37 as shown by the surface 39 in the cross-sectional view of FIG. 3(d). The formation of the sealed volume 36 would generate a relative vacuum in the sealed volume 36. When it is desired to further increase the relative vacuum (volume 36), the second sealed volume increasing layer 33 is removed, causing the size volume 36 to increase as shown by the surface 40, thereby increasing the level of vacuum inside the volume 36 as shown in FIG. 3(e).

Figure 4A:
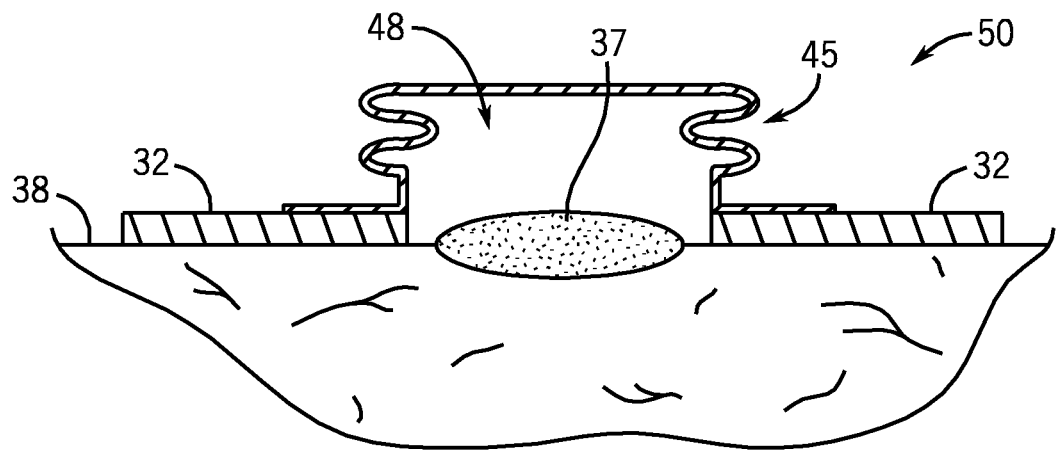
FIG. 4(a) illustrates the schematic of a cross-sectional view of the another embodiment of a blister dressing of FIG. 3(a) with a sealed volume forming layer constructed in a "bellow-like" configuration that has been released to form a volume with relative negative pressure over a blister.
Figure 4B:
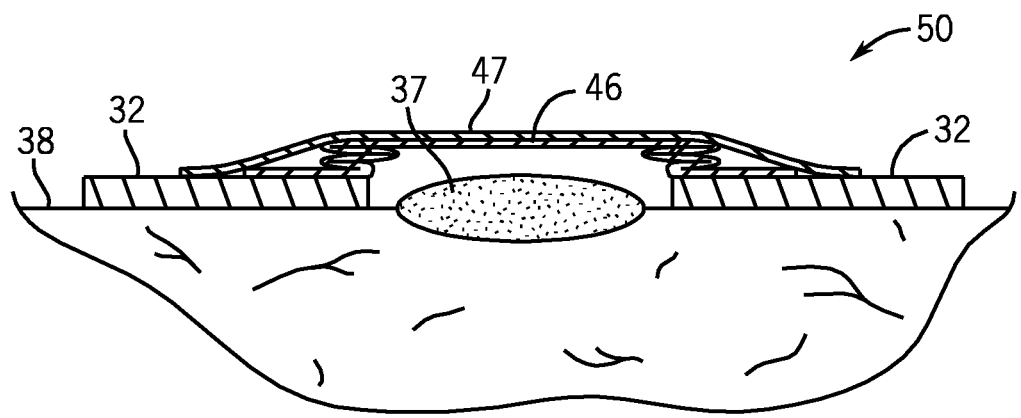
FIG. 4(b) illustrates the schematic of a cross-sectional view of the embodiment of the blister dressing of FIG. 4(a) before the "bellow-like" sealed volume forming layer has been released by at least one sealed volume increasing layer.

In another embodiment 50, which is otherwise similar to the embodiments 30 of FIG. 3(a), the sealed volume increasing layer (13 in FIGS. 1(b) and 2, 18 in FIG. 1(c), 21 in FIG. 1(d), and 35 in FIG. 3(b)), is constructed in a "bellows-like" structure 45 shown in FIG. 4(a), which is essentially "flattened" into the configuration 46 shown in FIG. 4(b) and held in this configuration by a sealed volume increasing layer 47, with a stored mechanical potential energy that when released would return to the configuration 45 (i.e., its original shape), thereby forming the volume 48 over the blister 37 area and generate a relative vacuum inside the volume 48 over the blister 37.

It will be appreciated by those skilled in the art that even though in the embodiment 50 of FIGS. 4(a) and 4(b) only one sealed volume increasing layer 47 was shown to be used, one may use more than one such sealed volume increasing layer as previously described for previous embodiments and use them similarly to sequentially increase the volume 48 over the blister 37 area and thereby increase the level of relative vacuum within the volume 48 and allow more fluid to be absorbed by the provided absorbent material (not shown in the schematics of FIGS. 4(*a*) and 4(*b*)).

Figure 5A:
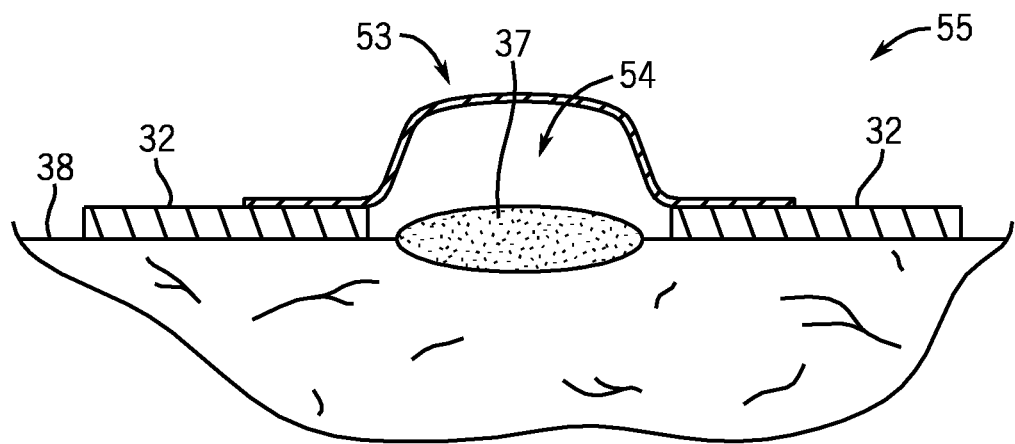
FIG. 5(a) illustrates the schematic of a cross-sectional view of the another embodiment of a blister dressing of FIG. 3(a) with a sealed volume forming layer constructed in a "circularly corrugated" configuration that has been released to form a volume with relative negative pressure over a blister.
Figure 5B:
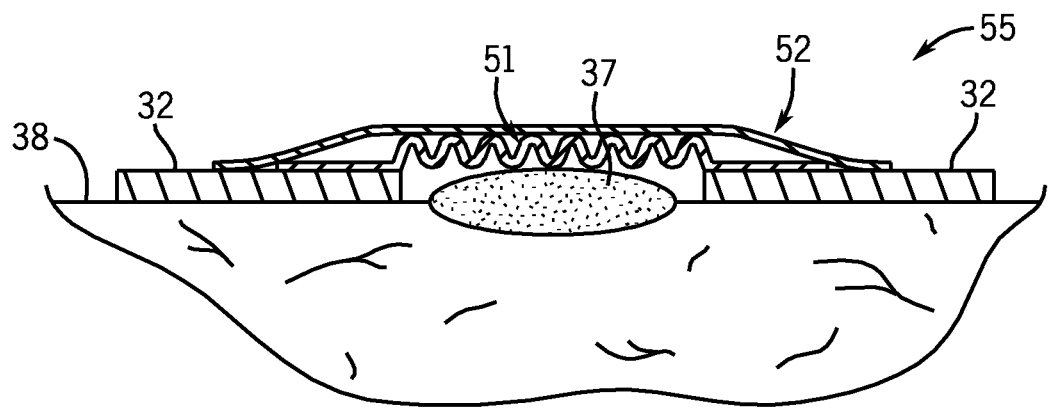
FIG. 5(b) illustrates the schematic of a cross-sectional view of the embodiment of the blister dressing of FIG. 5(a) before the "bellow-like" sealed volume forming layer has been released by at least one sealed volume increasing layer.

In another embodiment 55 shown schematically in FIGS. 5(*a*) and 5(*b*), which is otherwise similar to the embodiments 30 and 50 of FIG. 3(*a*) and FIG. 4(*a*), respectively, the sealed volume increasing layer is constructed in a "circularly corrugated" structure 51 shown in FIG. 5(*b*). In the blister dressing 55 and prior to its application to a blister area, the sealed volume increasing layer is essentially "flattened" into the configuration 51 shown in FIG. 5(*b*) and held in this configuration by a sealed volume increasing layer 52, with a stored mechanical potential energy that when released would return to its configuration 53 (i.e., its original shape) shown in FIG. 5(*a*), thereby forming the volume 54 over the blister 37 area and generate a relative vacuum inside the volume 54 over the blister 37.

It will be appreciated by those skilled in the art that even though in the embodiment 55 of FIGS. 5(*a*) and 5(*b*) only one sealed volume increasing layer 52 was shown to be used, one may use more than one such sealed volume increasing layers as previously described for previous embodiments of the present invention and use them similarly to sequentially increase the volume 54 over the blister 37 area and thereby increase the level of relative vacuum within the volume 54 and allow more fluid to be absorbed by the provided absorbent material (not shown in the schematics of FIGS. 5(*a*) and 5(*b*)).

It will also be appreciated by those skilled in the art that the mechanical potential energy may, at least partially, be stored in an element other than the pre-release (flattened) sealed volume forming layer (13 in FIGS. 1(*b*) and 2, 35 in FIGS. 3(*b*) and 3(*c*), 46 in FIGS. 4(*b*) and 51 in FIG. 5(*b*), and the like). The stored mechanical potential energy can then be released by the aforementioned sealed volume increasing layer such the layers 14 and 15 of the embodiment of FIG. 1(*b*), to deform the sealed volume forming layer into the desired shape, such as the one shown in FIGS. 2(*c*) and (2*d*) for the embodiment of FIG. 1(*b*). Such mechanical potential energy storing elements can take unlimited number of configurations and can be constructed using numerous materials with mechanical potential energy stored in them as strain energy or pressurized gas or the like and even as chemical energy, e.g., used to generate gasses in an enclosed volume. A few representative examples of such embodiments are presented below. However, it is noted that any other mechanical "deployable" mechanism known in the art with stored mechanical potential energy (in the form of strain energy or energy stored in the form of compressed gasses or gasses generated by a chemical reaction) may also be used. Hereinafter, the aforementioned mechanisms that provide at least part of the mechanical potential energy to cause the sealed volume forming layer to form an enclosed sealed volume (space) over the blister area is referred to as the "deploying mechanism".

Figure 6A:
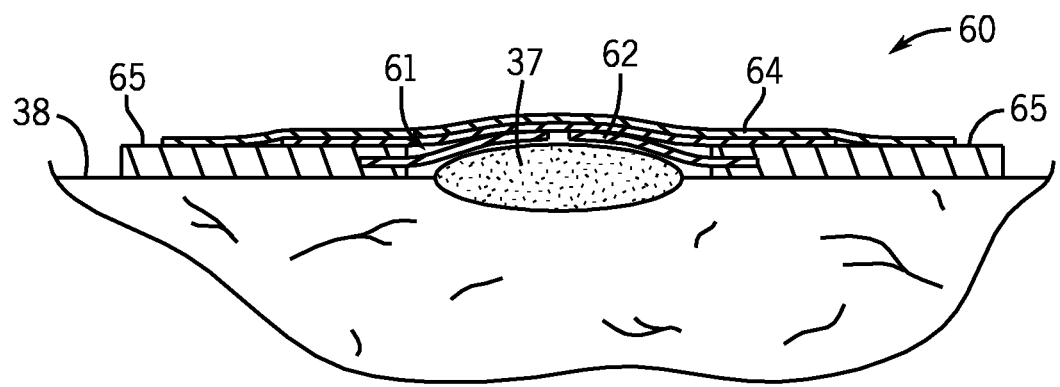
FIG. 6(a) illustrates the schematic of a cross-sectional view of an embodiment of a blister dressing with a sealed volume forming layer that is designed to deploy by a "deployable mechanism" once at least one sealed volume increasing layer is removed.
Figure 6B:
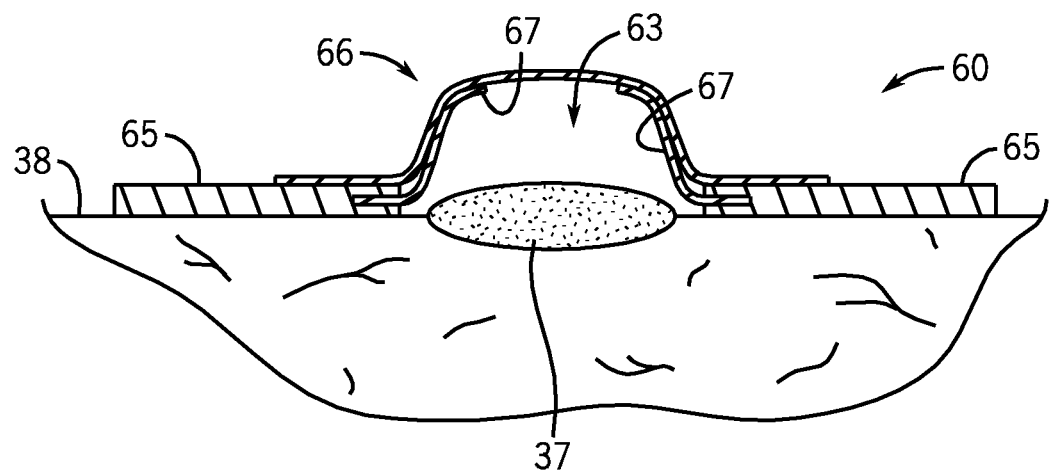
FIG. 6(b) illustrates the schematic of a cross-sectional view of an embodiment of the blister dressing of FIG. 6(a) after the sealed volume increasing layer has been removed and a sealed volume has been formed over the blister area.

The blister dressing embodiment 60 illustrated in the schematic of FIG. 6(*a*) is an example of a blister dressing that is provided with an aforementioned "deployable mechanism" 62. As can be seen in the schematic of FIG. 6(*a*), the embodiment 60 is similar to the previous embodiments except for its sealed volume forming layer 61 and the deploying mechanism 62 that is used to force the sealed volume forming layer 61 to deform to the shape 66 and provide a sealed volume 63 shown in FIG. 6(*b*) once the sealed volume increasing layer 64 (FIG. 6(*a*)) is removed. The deploying mechanism 62 shown in FIG. 6(*a*) consists of at least one flexural (bending) spring (preferably substantially flat) that are positioned substantially in the radial direction with one end fixed to the adhesive band section 65, preferably via a relatively rigid peripheral—circular in this case—element (not shown) to allow the aforementioned flexural spring elements to function as cantilever beams. In the configuration shown in FIG. 6(*a*), the aforementioned flexural beams of the deploying mechanism 62 are elastically "flattened" and are held in the flattened by the sealed volume increasing layer 64, thereby storing mechanical potential energy in the deploying mechanism for sealed volume 63 deployment. Once the sealed volume increasing layer 64 shown in FIG. 6(*a*) is removed, the flexural beams of the deploying mechanism 62 (two of which are seen in the schematic of the cross-sectional view of FIG. 6(*b*) and indicated by numerals 67) tend to return to their non-deformed configuration as shown in FIG. 6(*b*) by their stored mechanical potential energy, and thereby deform the sealed volume forming layer 61 shown in FIG. 6(*a*) to the shape 66 shown in FIG. 6(*b*).

In blister dressing embodiments using at least partially the aforementioned (sealed volume forming layer) deploying mechanisms, in its non-deployed configuration the sealed volume forming layer may be constructed by stretchable sheet of material such as latex, rubber or other available medical grade elastomeric material, and is then stretched by the elements (flexural elements in the case of the embodiment of FIGS. 6(*a*) and 6(*b*)) to form a sealed volume over the blister area. Alternatively, in its non-deployed configuration the sealed volume forming layer may be constructed by a flexible sheet that is folded to be packed into its non-deployed state, and is then deployed (unfolded) by the elements (flexural elements in the case of the embodiment of FIGS. 6(*a*) and 6(*b*)) to form a sealed volume over the blister area. In the latter case, the flexible sheet forming the sealed volume forming layer is preferably also at least partly stretchable to better deformable to the desired final shape.

It is appreciated by those skilled in the art that the aforementioned deploying mechanisms may also be used to assist the deployment of the previously described embodiments.

It will also be appreciated by those skilled in the art that the aforementioned deployable mechanisms can be constructed with the means of essentially locking their deploying elements (elements 62 and 67 for the embodiment 60 shown in FIGS. 6(*a*) and 6(*b*)) in their deployed configuration (configuration 67 for the embodiment 60 shown in FIGS. 6(*a*) and 6(*b*)). As a result, the volume formed by the sealed volume forming layer (volume 63 for the embodiment 60 shown in FIG. 6(*b*)) would resist certain amount of external pressure that might be accidentally be applied to the formed volume over the blister area.

Figure 7A:
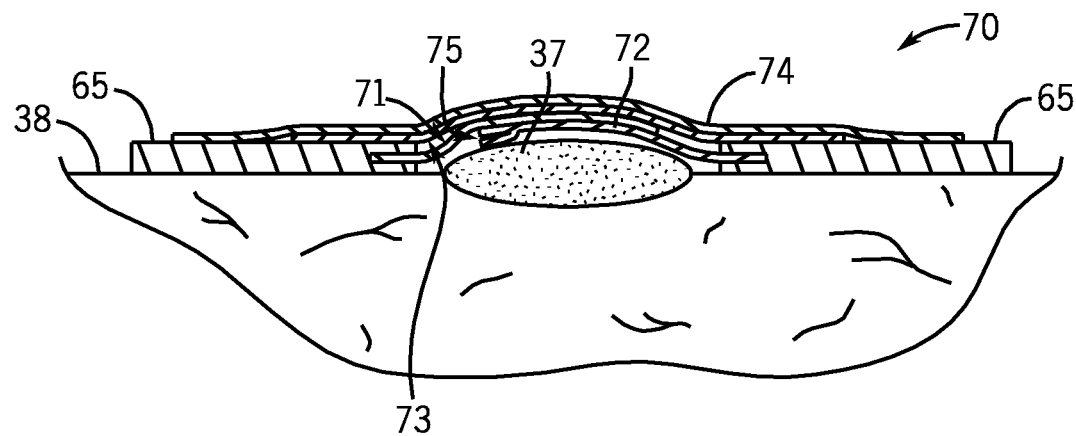
FIG. 7(a) illustrates a sectional view of another embodiment of blister dressing in an applied position.
Figure 7B:
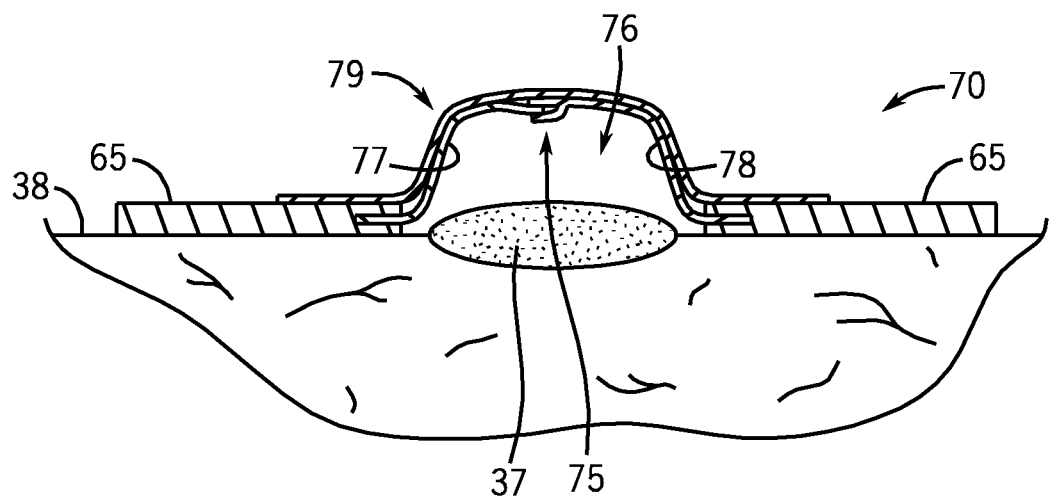
FIG. 7(b) illustrates a sectional view of the blister dressing of FIG. 7(a) in a deployed (volume forming) position.

An example of such deploying mechanisms with the aforementioned locking capability is illustrated in the embodiment 70 with the cross-sectional view of it shown in the schematics of FIGS. 7(*a*) and 7(*b*). The embodiment 70 is similar to that of the embodiment 60 but is provided with a deployment mechanism that essentially locks after deployment to resist pressure applied to the deployed (formed) sealed volume over the blister area as described below. The embodiment 70 is still applied to the surface of the skin 38 over the blister 37 area by the sealing adhesive band 65. The deploying mechanism consists of at least one pair of flexural (bending) spring (preferably substantially flat) elements 71 and 72, FIG. 7(*a*), which are positioned substantially in the radial direction with one end fixed to the adhesive band section 65, preferably via a relatively rigid peripheral—circular in this case—element (not shown) to allow the aforementioned flexural spring elements to function as cantilever beams. A "U" shaped end 75 is provided on the free end of the element 72. In the configuration shown in FIG. 7(*a*), the aforementioned at least one pair of flexural beams 71 and 72 of the deploying mechanism are elastically "flattened" and are held in the flattened by the sealed volume increasing layer 74, thereby storing mechanical potential energy in the deploying mechanism elements 71 and 72 for sealed volume 76 deployment, FIG. 7(*b*). Once the sealed volume increasing layer 74 shown in FIG. 7(*a*) is removed, the mechanical potential energy stored in the elements 71 and 72 of the deploying mechanism will tend to return them at least partially to their non-deformed configuration as shown in FIG. 7(*b*), seen in the schematic of the cross-sectional view of FIG. 7(*b*) as indicated by numerals 77 and 78, respectively, and thereby deform the sealed volume forming layer 73, FIG. 7(*a*), to the shape 79 shown in FIG. 7(*b*). The sealed volume forming layer 79 would thereby form a volume 76 with relative vacuum over the blister 37 area.

In another embodiment, the pre-release (flattened) sealed volume forming layer (13 in FIGS. 1(*b*) and 2, 35 in FIGS. 3(*b*) and 3(*c*), 46 in FIGS. 4(*b*) and 51 in FIG. 5(*b*), and the like) is at least partially (but preferably fully) retained by at least one "retaining element" that resists (and can prevent) the pre-release (flattened) sealed volume forming layer to return to its original shape (configuration). The user may then release the pre-release (flattened) sealed volume forming layer by removing the aforementioned "retaining elements". The retaining element may itself be held secured to the blister dressing (e.g., to the volume forming layer portion and/or the adhesive band) by an element similar to the aforementioned sealed volume increasing layers of the previous embodiments. Such "retaining elements" for partially or fully retaining the pre-release (flattened) sealed volume forming layer may be designed and constructed using many different methods known in the art and in many different ways, examples of which are provided below for illustrative purposes only and without limiting the present disclosure to their use.

Figure 8A:
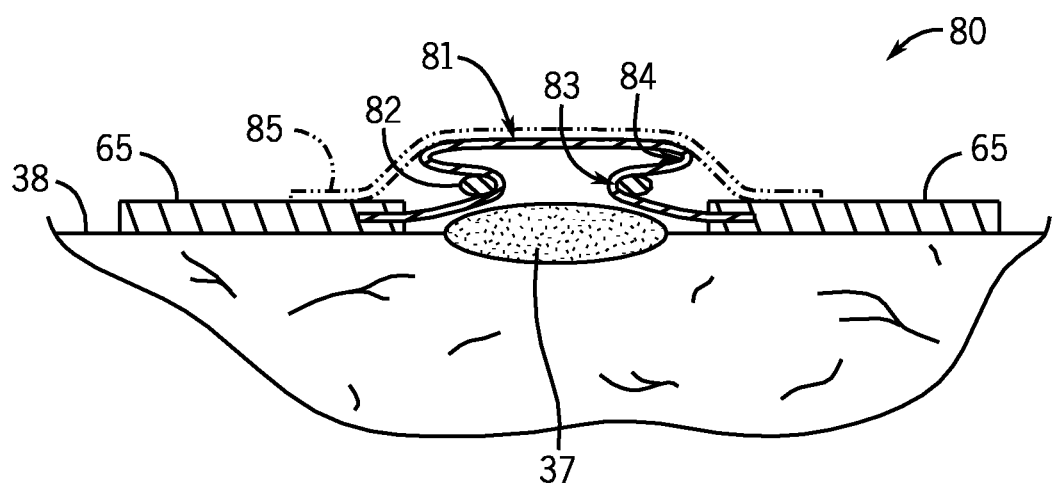
FIG. 8(a) illustrates a sectional view of another embodiment of blister dressing in an applied position.
Figure 8B:
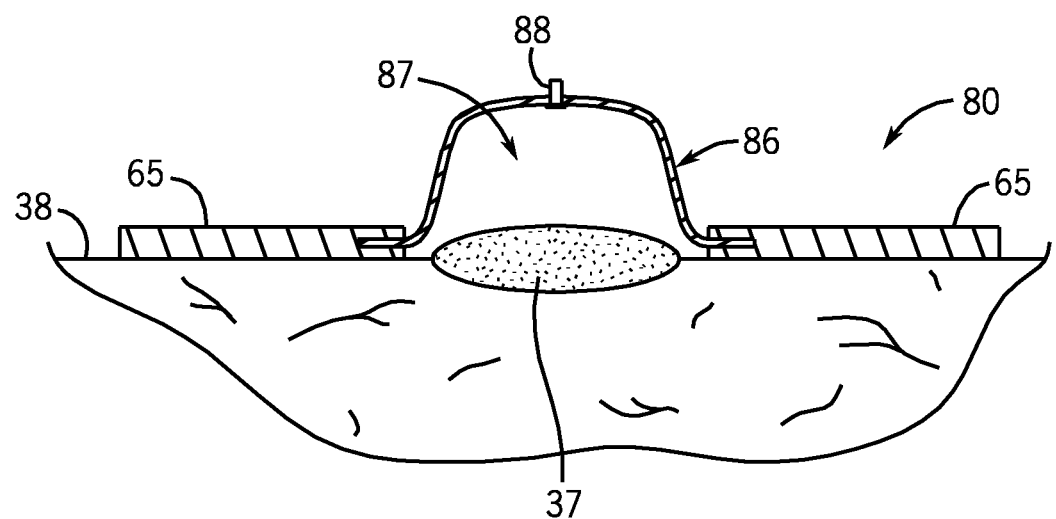
FIG. 8(b) illustrates a sectional view of the blister dressing of FIG. 8(a) in a deployed (volume forming) position.

In one such embodiment 80, shown in FIG. 8(*a*), the sealed volume forming layer 81 is held in its pre-release (flattened) configuration and with stored mechanical potential energy by a partial or full ring type retaining element 82. The blister dressing is otherwise similar to the embodiments of FIGS. 1-5, and is similarly applied to the surface of the skin 38 over the blister 37 area by the sealing adhesive band 65. When the retaining element 82 is a full (circular or non-circular) ring, the ring material need only to provide tensile strength and does not have to provide any rigidity, and may for example be a thread with enough tensile strength. The retaining ring mating surfaces 83 on the sealed volume forming layer 81 may be provided with the lips 84 to prevent the retaining element 82 from slipping out. The lips 84 or the like to prevent unwanted release of the sealed volume forming layer 81 are required if no additional means (such as the aforementioned sealed volume increasing layers) are provided. Minimal or no such lips 84 are required when additional means such as at least one aforementioned sealed volume increasing layer 85 is provided to prevent unwanted release of the sealed volume forming layer 81. When the retaining element 82 is an open "ring", then the ring has to be rigid and strong enough to withstand the forces applied to the ring by the ring mating surfaces 83. Once the blister dressing 80 is applied to the skin 38 over the blister 37 area, the user would remove/disengage/cut (depending on which one of the aforementioned alternative designs are used in the construction of the blister dressing) the retaining element 82, thereby allowing the sealed volume forming layer to be deployed and deform to the shape 86 shown in FIG. 8(*b*) and form a volume 87 with relative vacuum over the blister 37 area.

The use of retaining elements such as the element 82 shown in the schematic of FIG. 8(*a*) has the advantage of subjecting the sealed volume increasing layer to minimal (or no) force (when appropriately sized lips 84 are used), thereby making it easier for the sealed volume increasing layer to prevent untimely release (deployment) of the sealed volume forming layer.

It will be appreciated by those skilled in the art that in embodiments with retaining elements such as the embodiment 80 shown in the schematics of FIGS. 8(*a*) and 8(*b*), the mechanical energy may be partially of fully be stored in the aforementioned "deploying mechanisms" such as those described for the embodiments 60 and 70 of FIGS. 6(*a*)-6(*b*) and 7(*a*)-7(*b*), respectively.

It will also be appreciated by those skilled in the art that the aforementioned deploying mechanisms may be constructed, at least partially, with linkage-type of mechanisms with relatively rigid link components.

It will be appreciated by those skilled in the art that in all the above embodiments, the sealed volume forming layer may be kept (locked) in its pre-deployed ("flattened") configuration (e.g., 13 in FIGS. (1*b*) and (2), 35 in FIG. 3(*a*), 46 in FIG. 4(*b*), 51 in FIGS. 5(*b*) and 62 in FIG. 6(*a*)) or in its partially deployed configuration (e.g., 18 in FIGS. 1(*c*) and 39 in FIG. 3(*d*)) by at least one "retaining" element. The retaining element may in turn be kept in place by the sealed volume increasing layers and/or may be secured to the sealed volume forming layers and/or the adhesive bands described for the above embodiments.

It will be appreciated by those skilled in the art that all embodiments may also be provided with fluid absorbent layers (elements) such as the fluid absorbent layer 22 of the embodiment 10 of FIG. 2, which can be medicated for infection prevention purposes.

It will also be appreciated by those skilled in the art that all embodiments may also be provided with at least one sharp puncturing tip 23 over the surface under the volume forming layer, such as the sharp puncturing tips 23 of the embodiment 10 of FIG. 2. In addition, the area around the puncturing tip(s) of the fluid absorbent material layer may similarly be provided with local anesthetic medication so that the blister puncturing action becomes painless to the patient.

It will also be appreciated by those skilled in the art that all disclosed blister dressings can be provided with a protective and readily removed layer (preferably a medical grade plastic layer that is readily separated from the adhesive band—various types of which are well known in the art) before packaging. The assembled blister blessing is preferably sterilized and encased in a protective layer to maintain their sterilization.

It will also be appreciated by those skilled in the art that every one of the sealed volume forming layers of the disclosed embodiments may be provided with a port (such as the port 88 shown in the embodiment 80 of FIG. 8(*b*)) to allow the volume 87 of the deployed sealed volume forming layer 86 to be connected to an external vacuum source (not shown). The port 88 is preferably provided with a one-way valve so that when it is disconnected from the said external vacuum source, air and/or other contaminants would be prevented from entering the volume 87.

The port 88 can also be the type which allows puncturing by a needle which seals around the needle and reseals when the needle is removed (such as the ports used on medicament vials). Therefore, medicament, or other therapeutic agent such as saline etc., can be applied to the blister through the port or withdrawn from the volume through the port. A vacuum can also be applied though such port, such as by withdrawing the piston of a needle syringe which pierces the port. Such can be used to increase the vacuum in the volume or withdraw any fluids in the volume or introduced into the volume. Such a port can be used on any of the embodiments described herein.

Figure 9A:
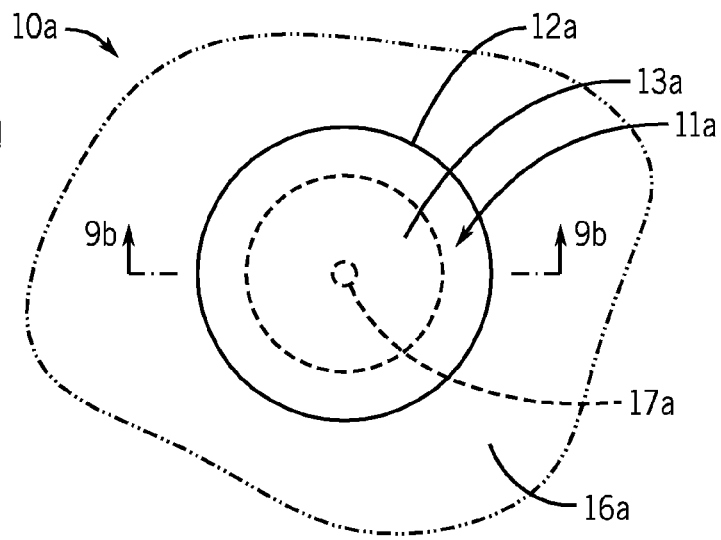
FIG. 9(a)-9(c) illustrate a variation of the embodiment of FIGS. 1(a)-1(d).
Figure 9B:
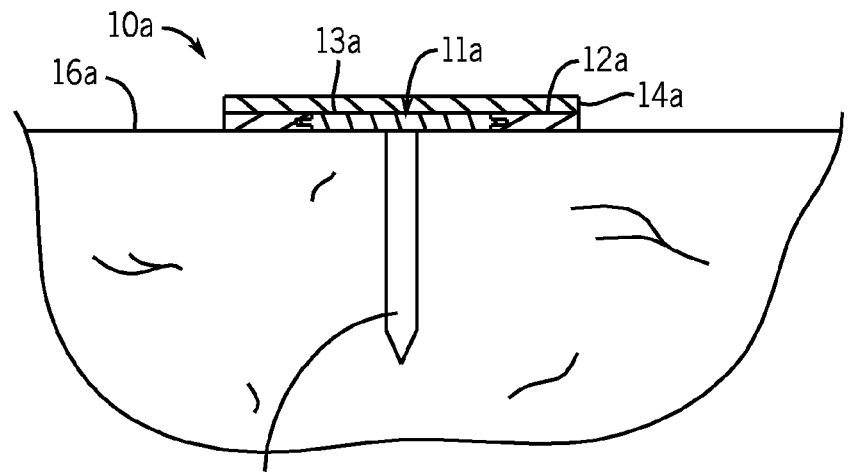

A schematic of a variation of the dressing shown in FIGS. 1(a) to 1(d) will now be described with regard to FIGS. 9(a)-9(c), generally referred to by reference numeral 10a and in which like reference numerals refer to like features. In FIG. 9(a), a top view of the dressing embodiment 10a is shown. It is noted that the circular shape of the dressing and an adhesive band section 12a are shown to be circular for presentation only and may take any other appropriate shape. The dressing 10a consists of a pressure applying section 11a, which is surrounded by the adhesive "band" 12a. The cross-sectional view of the dressing 10a is shown in FIG. 9(b). The pressure applying section 11a is shown to consist of a pressure applying layer 13a similar to that shown and described with regard to the dressing of FIGS. 1(a)-1(d). The pressure applying layer 13a is shown schematically in FIGS. 9(a)-9(c) for the sake of brevity. However, those skilled in the art would understand how to construct the same based on the description with regard to FIGS. 1(a)-1(d). A layer 14a is also provided, also similar to that shown and described with regard to the dressing of FIGS. 1(a)-1(d). More than one layer 14a can be provided, such as the two layers (14 and 15) discussed with regard to the dressing of FIGS. 1(a)-1(d). The layer 14a is attached to the pressure applying layer 13a using any method known in the art, such as with adhesives, so that the user could readily separate them. The adhesive band 12a is permanently attached to the periphery of the pressure applying layer 13a using any method known in the art and may have a slight overlap to provide enough strength so that as the pressure applying layer deforms to apply normal pressure to the wound, the integrity of the dressing 10a is ensured. When being used on a patient, the pressure applying layer 13 is placed over a wound, such as a puncture 17a, and the adhesive band 12a of the blister dressing 10a is attached to the surface of the skin 16a.

Figure 9C:
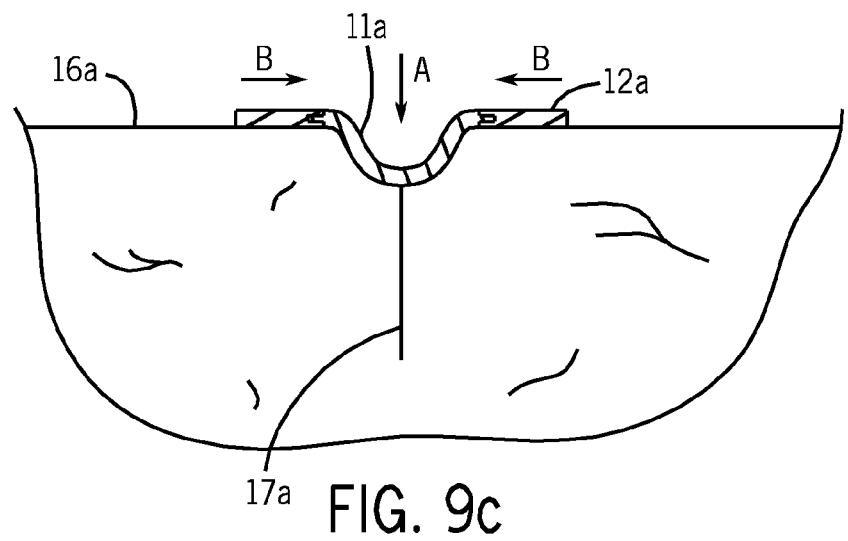

In the schematics of FIGS. 9(a)-9(c), for the sake of simplicity, only one distinct layer 14a is used. However, two or more than two such layers with different preloading patterns can be utilized in the construction of the dressing. In addition, the blister dressing assembly 10a does not have to be initially flat, and may assume any appropriate shape and configuration as dictated with the particular application. For example, the blister dressing assembly 10a may have a slight concavity (curved downward toward the skin) so that when the restraint is removed from the pressure applying layer 13, the same will deform downwards to apply the normal pressure to the skin and wound.

Once the blister dressing 10a is applied to the skin 16a over the puncture 17a and the adhesive band 12a is attached over the skin, the layer 14a may be removed to release a restraint on the pressure applying layer 13a to deform the same such that it curves inward toward the skin in the direction of arrow A. Thus, once the layer 14a is removed, the mechanical potential energy stored in the pressure applying layer 13a is released as described above, allowing the pressure applying layer 13a to take an inverted dome-shaped as shown in FIG. 19(c), thereby applying pressure to the wound, so as to facilitate a reduction or elimination of bleeding from the puncture wound 17a. Thus, the dressing 10a operates similarly to that of the dressing 10 shown in FIGS. 1(a)-1(d) except that the central portion thereof is configured to curve downward into the skin to apply a normal force to the wound.

The dressing 10a may also be formed of an elastic material, such as at the adhesive band 12a, that is also restrained in a larger size by the layer 14a. Thus, when the layer 14a is removed, not only is the restraint removed from the pressure applying layer 13a, but also from the elastic material, thus also applying a closing force on the puncture wound 17a in the direction of arrows B.

The embodiments of FIGS. 9(a)-9(c) have general utility for many types of wounds but may have particular utility for puncture wounds, such as those associated with needle wounds (e.g., from giving blood, having bloodwork, getting a transfusion, puncture stab wounds, etc.). For such wounds, the dressing 10a applies pressure in the direction of arrow A to reduce or eliminate blood flow from the wound and may be further configured to apply pressure to the wound in the direction of arrows B to close the wound, further reducing blood flow and promoting proper healing.

Figure 10A:
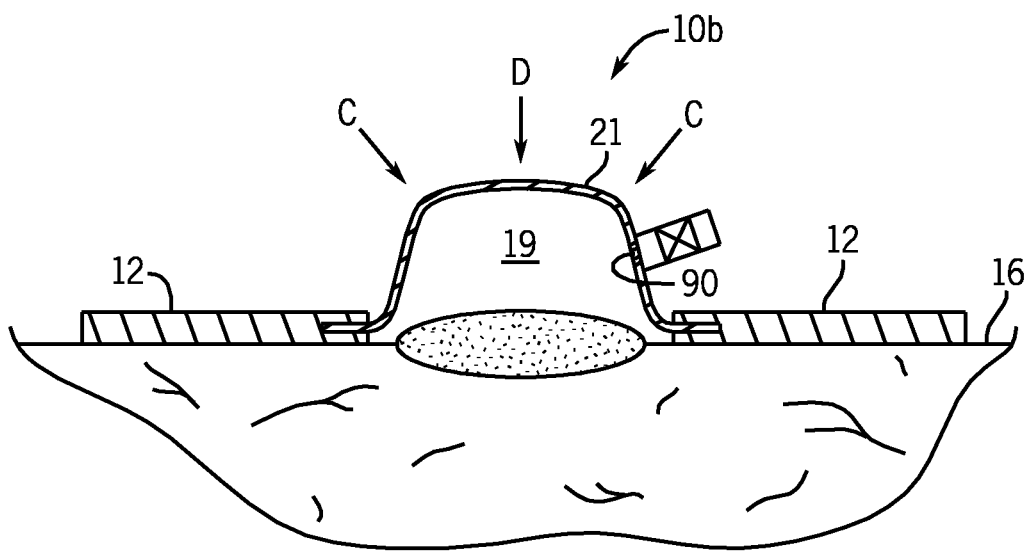
FIGS. 10(a) and 10(b) illustrate variations of the embodiment of FIGS. 1(a)-1(d).

Referring now to FIG. 10(a), there is shown another variation of the blister dressing of FIGS. 1(a) to 1(d), generally referred to by reference numeral 10b and in which like reference numerals indicate like features. In the blister dressing 10b, the sealed volume forming layer 21 includes a port 90 having a one-way valve 92 in communication therewith. The port 90 can be an opening in the sealed volume forming layer 21 with a connected portion of tubing and the one-way-valve 92, such as a duck bill valve, disposed in or on the tubing. Alternatively, the one-way valve 92 can be directly affixed to the port 90. With such an arrangement, the sealed volume forming layer 21 can be flexible and depressed, such as by squeezing in the direction of arrows A or pushing down in the direction of arrow B. Thus, the space 19 within the sealed volume forming layer 21 can be evacuated or further evacuated to promote healing as discussed above.

Figure 10B:
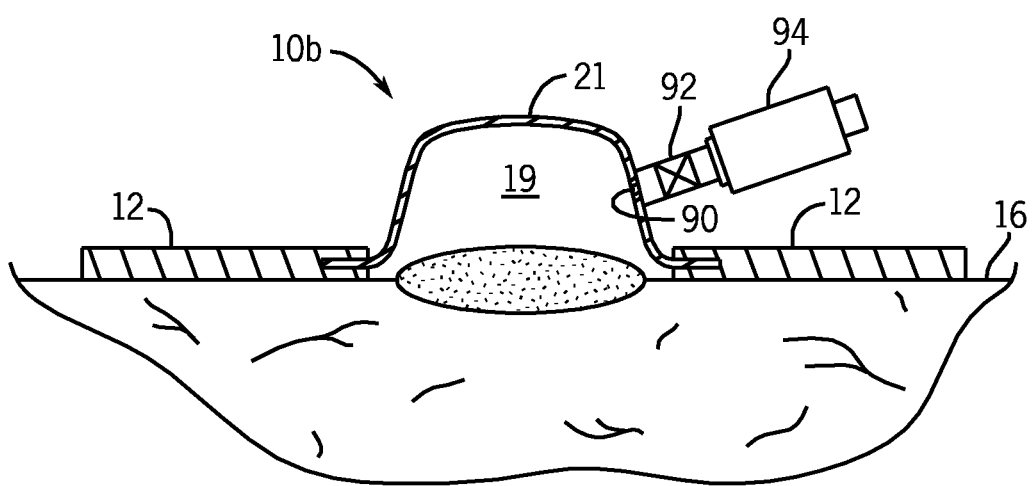

FIG. 10(b) illustrates a variation of the blister dressing of FIG. 10(a) in which a vacuum source 94 is provided in communication with the port 90 and one-way valve 92, such as being disposed on the tubing. The vacuum source 94 can be a small pump, such as a bellows that can be squeezed, a syringe that can be withdrawn or a connection to a centralized vacuum source (as is typical in hospital settings).

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A dressing for application to a wound on skin, the dressing comprising:
a first member having an unrestrained shape, the unrestrained shape of the first member comprises at least a portion of the first member having a concavity relative to a surface of the skin such that a central portion of the first member in the unrestrained shape is closer to the surface of the skin than other portions of the first member in the unrestrained shape, the first member further having an adhesive disposed on a first surface;

a second member for restraining the first member in a restrained shape different from the unrestrained shape, the second member being removably attached to the first member on a second surface of the first member, the second surface being different from the first surface;

wherein removal of the second member from the first member after the first member is adhered to the skin causes the first member to change towards the unrestrained shape such that the portion of the first member having a concavity applies a normal force substantially perpendicular to the surface of the skin.

2. The dressing of claim 1, wherein at least the first member is circular in shape.

3. The dressing of claim 2, wherein the adhesive is disposed on the first surface in an annular pattern.

4. The dressing of claim 1, wherein the restrained shape is substantially planar.

5. A method for closing a puncture wound on skin, the method comprising:

adhering a first surface of a first member having an unrestrained shape to the skin and over the puncture, the unrestrained shape of the first member comprises at least a portion of the first member having a concavity relative to a surface of the skin such that a central portion of the first member in the unrestrained shape is closer to the surface of the skin than other portions of the first member in the unrestrained shape; and subsequent to the adhering, removing a second member for restraining the first member in a restrained shape from the first member;

wherein the removal of the second member from the first member causes the first member to change towards the unrestrained shape such that the portion of the first member having the concavity applies a normal force substantially perpendicular to the surface of the skin.

6. The method of claim 5, wherein the removing further causes a force substantially perpendicular to the normal force which tends to close the puncture wound.

* * * * *